United States Patent [19]

Peppmöller et al.

[11] Patent Number: 5,304,664
[45] Date of Patent: Apr. 19, 1994

[54] PROCESS FOR THE PRODUCTION OF HIGHLY SULFATED FATTY ACIDS AND FATTY ACID DERIVATIVES

[75] Inventors: Reinmar Peppmöller, Krefeld; Kurt Dahmen, Mönchengladbach-Rheydt, both of Fed. Rep. of Germany

[73] Assignee: Chemische Fabrik Stockhausen GmbH, Krefeld, Fed. Rep. of Germany

[21] Appl. No.: 681,495
[22] PCT Filed: Oct. 20, 1989
[86] PCT No.: PCT/EP89/01257
    § 371 Date: Apr. 5, 1991
    § 102(e) Date: Apr. 5, 1991
[87] PCT Pub. No.: WO90/04586
    PCT Pub. Date: May 3, 1990

[30] Foreign Application Priority Data
Oct. 20, 1988 [DE] Fed. Rep. of Germany ....... 3836447

[51] Int. Cl.$^5$ ............................................. C07C 303/00
[52] U.S. Cl. ...................................................... 554/98
[58] Field of Search ............... 260/399; 554/100, 98, 554/97, 99

[56] References Cited

U.S. PATENT DOCUMENTS 2,127,641 8/1938 Cremer ................................ 554/100
4,545,939 10/1985 Sekiguchi et al. ................... 554/98

*Primary Examiner*—José G. Dees
*Assistant Examiner*—Deborah D. Carr
*Attorney, Agent, or Firm*—Sprung, Horn, Kramer & Woods

[57] ABSTRACT

To obtain highly sulfated fatty acids, hydroxy fatty acids or oxalkylated hydroxy fatty acids, the reaction mixture obtained from the sulfatation of unsaturated fatty acid esters and/or saturated hydroxy fatty acid ester and/or oxalkylated hydroxy fatty acid esters is neutralized, optionally separated from the brine, diluted with water and hydrolyzed at a temperature between 20° C. and 160° C. after addition of lye the amount of which at maximum is equivalent to the organically bonded sulfuric acid content. After phase separation from the non-sulfated starting products, the highly sulfated fatty acids are isolated from the aqueous phase.

13 Claims, No Drawings

PROCESS FOR THE PRODUCTION OF HIGHLY SULFATED FATTY ACIDS AND FATTY ACID DERIVATIVES

The present invention relates to a process for the production of highly sulfated fatty acids, hydroxy fatty acids and/or oxalkylated hydroxy fatty acids.

The reaction of fatty acids and fatty acid esters with sulfuric acid or oleum to manufacture water-soluble products or those which have surface active properties is a wide-spread method in industry. Starting, for example, from castor oil, olive oil, soybean oil, sunflower oil, tallow, or various fish oils, as well as the natural fatty acids bonded therein and obtainable by saponification, and depending on certain reaction conditions so-called "sulfated oils" for many purposes could be manufactured.

A particularly known example of this family is sulfated castor oil which is commercially available until today under the name "Turkey-red oil".

According to a process described in DRP 561 715, it is possible to produce products with an extraordinary resistance to acids and salts by means of short-time sulfatation with large amounts of sulfuric acid under rapid cooling. Analytic tests revealed that these extraordinary wetting agents exhibited an amount of organically bonded sulfur which was substantially higher than could be achieved with other processes.

According to these results efforts were made to achieve a degree of sulfatation which is as high as possible. The degree of sulfatation indicates how much percent of the fatty acids within the examined product are actually sulfated; in this connection, it is arbitrarily assumed that the total amount of organically bonded sulfuric acid (calculated as $SO_3$) is present in the form of ricinoleic acid monosulfuric acid ester (H. P. Kaufmann, Analyse der Fette und Fettprodukte [Analysis of the fats and fat products], Springer Verlag 1958, page 1495). Due to the properties with respect to application technology a sulfatation degree of at least 50 % was, and still is desirable. The terms "highly sulfated" or "high degree of sulfatation" will be used to this effect in the following.

According to known processes, increasing the sulfatation degree to values of more than 50 % requires the use of solvents, such as trichloroethylene. In this connection, the solvent on the one hand serves as diluent during sulfation, and, on the other hand, as agent to separate off the non-sulfated portions from the reaction product.

DE-OS 36 06 868 describes a possibility to separate the unsulfated portions from the sulfation mixture without having to use a solvent. According to this publication, foreign substances having a demulsifying effect are added during the production of unsaturated fatty-acid-low-alkyl-ester-sulfonates. It is recommended to use additions at 5 to 400 parts by weight of sorbitan- or glycerol fatty acid ester and 5 to 300 parts by weight of a low-molecular alcohol per 100 %-wt. sulfonated ester.

It is accordingly the object of the present invention to provide a process for the production of highly sulfated fatty acids, hydroxy fatty acids and/or oxalkylated hydroxy fatty acids, which on the one hand permits to avoid the use of solvents, the toxicity problems associated therewith, and the expenditure arising with respect to devices and equipment, and which, on the other hand, can do without the addition of foreign substances which may impair the end products' properties with respect to application technology.

This object is achieved by the process according to the present invention, in which—subsequent to the sulfation which is known per se—the reaction mixture comprising the sulfated esters as well as unsulfated starting products is neutralized. Then the neutral ester sulfate is diluted with water, in this connection the brine may optionally be separated off first. After addition of lye whose quantity is equimolar or submolar to the organically bonded sulfuric acid content, the alkaline solution obtained is hydrolyzed at temperatures between 20° C. and 160° C., preferably between 40° and 90° C., whereby a water-insoluble oil layer consisting of unsulfated esters separates out of the aqueous phase comprising the desired sulfated fatty acids which can subsequently be isolated.

The ester sulfate obtained from the sulfation reaction and normally adjusted to neutral is preferably diluted with at least half of the weight amount of water, further preferred double or triple the weight amount of water, relative to the weight of the estersulfate-mixture.

The water content of the alkaline mixture at the beginning of the hydrolysis advantageously amounts to 60 to 95 %-wt, preferably 70 to 90 %-wt, relative to the total mixture.

According to the present invention, the ester sulfate mixture which is optionally desalinated may be mixed with 10 to 50 %-wt. of an already hydrolyzed ester sulfate, relative to the non-hydrolyzed ester sulfate, and subsequently subjected to further hydrolysis at temperatures of at least 20° C. Hydrolysis may be carried out under pressure or without pressure.

Suitable starting products are unsaturated fatty acid esters, saturated or unsaturated hydroxy fatty acid esters, or the alkoxylation products of saturated or unsaturated hydroxy fatty acid esters of water-soluble mono- or bivalent alcohols, such as methanol, ethanol, n-propanol, i-propanol, ethylene glycol, 1,2-propylene glycol, 1,3-propylene glycol, 1,4-butylene glycol, and hexylene glycol.

Easily accessible fatty acid esters are preferred, such as oleic acid methyl ester, tall oil fatty acid methyl ester, fish oil fatty acid methyl ester, rapeseed oil fatty acid methyl ester, oleic acid ethyl ester, oleic acid isopropyl ester, ethylene glycol dioleate, 1,2-propylene glycol dioleate, ricinoleic fatty acid methyl ester, ricinoleic fatty acid ethyl ester, and the alkoxylated derivatives of the ricinoleic fatty acid ester—provided that they are water-insoluble.

The mentioned starting products may be used alone or in admixture and are preferably substantially free from fatty acids.

Depending on their origin the starting esters contain portions of unsulfatable saturated esters which, however, do not disturb the process according to the present invention, they can be isolated together with the unsulfated unsaturated esters from the desired sulfated products.

However, free fatty acids and soaps may impair the production process according to the present invention. For this reason, fatty acid esters with the lowest possible cleavage should be used in cases where very high separation efficiency is required.

The achieve degree of sulfatation is of no great importance in the reaction of these esters with sulfuric acid or oleum to the ester sulfates. The reaction may be carried out according to common methods.

The step of dilution according to the present invention under the addition of bases results in phase separation into an upper, oily phase and a lower, aqueous phase comprising the desired sulfated fatty acids. The upper oil-phase, called "neutral oil", mainly comprises unsulfated esters.

Any lye suitable for the cleavage of fats can be used in the alkaline saponification, in particular strong lyes, such as soda lye and potash lye. Since the fatty acid ester sulfates are readily saponifiable, the use of weaker bases, such as ammonia and amines, is possible too.

The amount of lye depends on the desired portion of sulfated soap and alcohol in the ester sulfate solution, and can freely be selected between a 10% and 100% cleavage of the ester sulfate.

The alkali treatment in the presence of larger amounts of water according to the present invention nearly exclusively results in a saponification of the fatty acid ester sulfate.

If at all, hydrolysis of unsulfated portions of the mixture takes place to a negligible extent.

The alkaline solution is heated to a temperature between 20° C and 160° C. preferably between 40° and 90° C., until the lye is exhausted and the unsulfated portions separate off in form of the upper natural oil film.

An amount of lye larger than the equivalent to the organically bonded sulfuric acid content is to be avoided, since in case of lye excess of unsulfated ester would be cleaved too. This undesired saponification can be avoided by the addition of sub-stoichiometric amounts of lye. If the ester sulfate mixture obtained from the sulfation reaction is to be stored intermediately, it may be of advantage to effect an alkaline stabilization by a slight excess of lye when the acidic ester sulfate is set to neutral, so as to avoid an uncontrolled acidic cleavage. This excess of lye must be considered when the lye is added later so that the total quantity added does not exceed an amount equivalent to the organically bonded sulfuric acid content. During the saponification reaction the aqueous solution of the sulfatation mixture which—depending on the sulfatation degree—is clear or milky increasingly becomes cloudy, and finally oil separates out. The phase separation can be accelerated physically, e.g., by means of centrifuges or packed columns.

The period of time until the oil separation starts mainly depends on the kind of fatty acid ester, the inorganic salt content, and the temperature during the treatment. Whereas sulfated esters of primary alcohols rapidly separate the unsulfated portions during the process according to the present invention, the separation in case of sulfated esters of bivalent alcohols takes place slowlier; the latter having a stronger tendency to permanently absorb the natural oil portions. Depending on the desired result in each individual case, an optimation of the process can be achieved by variation of the temperature and—via the lye amount—the degree of saponification.

However, it is possible too, and sometimes ever recommendable to mix a slow-reacting sulfated ester with a quick-reacting ester, e.g., a sulfated methyl ester. The additionally added sulfated ester may be the same or different with respect to the fatty acid base and/or degree of sulfatation.

It is of advantage with respect to the subsequent hydrolysis and phase separation to use the additional es-ter suitable therefor directly in the sulfatation reaction so that a mixture already comprising different suitable esters is sulfated and subsequently subjected to the further steps according to the present invention.

The individual stages of the process according to the present invention may be carried out either discontinuously or continuously. In case of short-time heating of the alkaline ester sulfate solution under pressure, e.g., within a tubular or a falling-film reactor, the required saponification temperature is to be adapted to the reactor arrangement and the flow rate. In this connection, the rule applies that a reduction of the residence time of the ester sulfate solution within the heating device requires an elevation of the saponification temperature.

The process according to the present invention shall be illustrated by way of the following examples which are given in the form of general working instructions I to IV and the corresponding tables.

General Working Instruction I

A g of an ester sulfate or ester sulfate mixture, respectively, manufactured with concentrated sulfuric acid and neutralized with soda lye and having a degree of sulfatation $S_1$ at a $SO_3$-content of B%, were diluted with 2,000 ml softened water. Subsequently, 45% soda lye the amount of which was equimolar to the $SO_3$-content was added (quantity C). After strong mixing, the alkaline solution was heated to approximately 50° C., whereby the solution became very turbid, and finally layers formed. Phase separation resulted in D g unsulfated fatty acid ester.

The sulfated fatty acid sulfate was obtained from the lower, aqueous phase after addition of mineral acid (pH=4) and common salt. The degree of sulfatation of the starting products and that of the end products ($S_1$ and $S_2$) are indicated in Table 1.

In examples h and i hydrolysis was carried out with 45% potash lye and concentrated ammonia solution, respectively.

General Working Instruction II

A g of an ester sulfate or ester sulfate mixture, respectively, produced with concentrated sulfuric acid and neutralized with soda lye and having a degree of sulfatation $S_1$ at an $SO_3$-content of B%, were diluted with 2,000 ml softened water. Subsequently, 45% soda lye (quantity C) was added the amount of which was submolar with respect to the $SO_3$-content. Further processing was carried out as described under I.

The test results are summarized in Table II.

General Working Instruction III

A g ester sulfate or ester sulfate mixture, respectively, manufactured with concentrated sulfuric acid and neutralize with soda lye having a degree of sulfatation $S_1$ at an $SO_3$-content of B%, were diluted with 400 ml boiling, softened water. Subsequently, the mixture was heated to 80° C. and an equimolar amount (relative to the $SO_3$-content) of 45% soda lye (quantity C) was added. After strong mixing, the alkaline, cloudy liquid was placed in a centrifuge and centrifuged at 3,000 rmp for 3 minutes (Martin Christ, Osterode; type UJ3, 330 watts). Finishing was carried out as specified under I.

The results are shown in Table III.

The manufacture of the starting material which builds the basis for the general working instructions I, II, and III is exemplified on the basis of the oleic acid methyl ester:

538 g oleic acid methyl ester (Edenor ME TI 05, HENKEL) were sulfated within 1 hour with 350 g concentrated sulfuric acid under ice cooling (max. 10° C.) and rapid stirring. Subsequently, 1675 g of an alkaline-aqueous solution comprising 225 g caustic soda and 120 g common salt were added as quickly as possible in order to neutralize the solution to a pH-value of 5 to 6 and work it up. In this concentration, the temperature rose to 80° C. The mixture was allowed to stand at 50° to 60° C., subsequently the salt solution was removed and the obtained ester sulfate was determined with respect to water content and sulfatation degree (yield: 1,000 g).

| Water content: | 40% |
|---|---|
| Content of effective substance: | 60% |
| Degree of sulfatation: | appr. 50% |

This product was subjected to the processes according to the general working instructions I (examples h, i), II (examples b, c, d), and III (example a). In this connection, unsulfated methyl ester was separated from the aqueous phase and the sulfatation degree increased correspondingly.

General Working Instruction IV

According to the general working instruction I, A g of an ester sulfate produced with concentrated sulfuric acid and neutralized with soda lye and having an $SO_3$-content of B% and a sulfatation degree of $S_1$% are diluted with 500 ml softened water. Hydrolysis and further working up were carried out according to the general working instruction I.

The results are shown in Table IV.

TABLE I

General working instruction I

| | | Charge (g) A | $H_2O$-addition (g) | Ratio A:$H_2O$ | $H_2O$-content (%)* | $SO_3$ (%) B | (g) C | Unsulf. (g) D | $S_1$ (%) | $S_2$ (%) |
|---|---|---|---|---|---|---|---|---|---|---|
| | | | | | | | NaOH 45% | | | |
| a) | Oleic acid methyl ester | 1,000 | 2,000 | 1:2.0 | 80.0 | 8.2 | 90 | 201 | 57 | 87 |
| b) | Tall oil fatty acid methyl ester | 1,134 | 2,000 | 1:1.76 | 78.3 | 8.6 | 108 | 182 | 58 | 82 |
| c) | Oleic acid isopropyl ester | 796 | 2,000 | 1:2.51 | 82.9 | 9.5 | 82 | 151 | 56 | 83 |
| d) | 1,2-propylene glycol dioleate | 984 | 2,000 | 1:2.03 | 80.2 | 7.7 | 84 | 106 | 48 | 61 |
| e) | Ricinoleic acid methyl ester | 1,346 | 2,000 | 1:1.49 | 75.8 | 7.1 | 106 | 470 | 39 | 71 |
| f) | Oxyethylated ricinoleic acid methyl ester (3 mole EO) | 984 | 2,000 | 1:2.03 | 80.2 | 6.1 | 66 | 130 | 41 | 76 |
| g) | Oleic acid methyl ester oleic acid isopropyl ester (mixed 1:1) | 1,000 | 2,000 | 1:2.00 | 80.0 | 8.4 | 93 | 193 | 57 | 85 |
| | | | | | | | KOH 45% | | | |
| h) | Oleic acid methyl ester | 1,500 | 2,000 | 1:1.33 | 74.3 | 4.8 | 112 | 145 | 50 | 89 |
| | | | | | | | $NH_3$ conc. | | | |
| i) | Oleic acid methyl ester | 1,500 | 2,000 | 1:1.33 | 74.3 | 4.8 | 106 | 65 | 50 | 68 |

*$H_2O$-content prior to hydrolysis, relative to an average water content of the starting product of 40%.

TABLE II

General working instruction II

| | | Charge (g) A | $H_2O$-addition (g) | Ratio A:$H_2O$ | $H_2O$-content (%)* | $SO_3$ (%) B | NaOH, 45% (g) C | Unsulf. (g) D | $S_1$ (%) | $S_2$ (%) |
|---|---|---|---|---|---|---|---|---|---|---|
| a) | Oleic acid methyl ester | 750 | 2,000 | 1:2.67 | 83.6 | 8.2 | 41 | 229 | 43 | 81 |
| b) | " | 1,000 | 2,000 | 1:2.00 | 80.0 | 4.8 | 21 | 79 | 50 | 80 |
| c) | " | 1,000 | 2,000 | 1:2.00 | 80.0 | 4.8 | 16 | 68 | 50 | 76 |
| d) | " | 1,000 | 2,000 | 1:2.00 | 80.0 | 4.8 | 11 | 52 | 50 | 70 |

*$H_2O$-content prior to hydrolysis relative to an average water content of the starting product of 40%.

TABLE III

General working instruction III

| | | Charge (g) A | $H_2O$-addition (g) | Ratio A:$H_2O$ | $H_2O$-content (%)* | $SO_3$ (%) B | NaOH, 45% (g) C | Unsulf. (g) D | $S_1$ (%) | $S_2$ (%) |
|---|---|---|---|---|---|---|---|---|---|---|
| a) | Oleic acid methyl ester | 300 | 400 | 1:1.33 | 74.3 | 4.8 | 16 | 28 | 50 | 88 |

*$H_2O$-content prior to hydrolysis relative to an average water content of the starting product of 40%.

TABLE IV

| | | Charge (g) A | $H_2O$-addition (g) | Ratio A:$H_2O$ | $H_2O$-content (%)* | $SO_3$ (%) B | NaOH, 45% (g) C | Unsulf. (g) D | $S_1$ (%) | $S_2$ (%) |
|---|---|---|---|---|---|---|---|---|---|---|
| a) | Oleic acid methyl ester | 1,000 | 500 | 2:1 | 60 | 8.2 | 90 | 108 | 57 | 78 |

*$H_2O$-content prior to hydrolysis relative to an average water content of the starting product of 40%.

We claim:
1. A process for the production of a highly sulfated fatty acid, hydroxy fatty acid or oxyalkylated hydroxy fatty acid consisting essentially of
sulfating at least one of an unsaturated fatty acid ester and a saturated or unsaturated hydroxy fatty acid ester or oxyalkylated saturated or unsaturated hydroxy fatty acid ester,
neutralizing the reaction mixture,
optionally separating the resulting brine,
diluting the neutral or alkaline stabilized ester sulfate with water,
adding lye in an amount which is at most equimolar to the organically bonded sulfuric acid content, hydrolyzing the alkaline solution at a temperature between 20° C. and 160° C., separating the resulting oil-phase which substantially consists of non-sulfated starting product from the aqueous phase which comprises the highly sulfated fatty acids, and isolating and highly sulfated fatty acid.

2. The process according to claim 1, wherein dilution of the neutralized, optionally desalinated ester sulfate mixture is effected with at least half of the weight amount of water, relative to the weight of the sulfation mixture.

3. The process according to claim 1, wherein the neutral, optionally desalinated ester sulfate mixture is diluted with double to triple its weight of water.

4. The process according to claim 1, wherein the water content of the alkaline mixture at the beginning of the hydrolysis amounts of 60 to 95%-wt, relative to the total mixture.

5. The process according to claim 1, wherein the water content of the alkaline mixture at the beginning of the hydrolysis amounts to 70 to 90%-wt. relative to the total mixture.

6. The process according to claim 1, wherein the optionally desalinated ester sulfate mixture is mixed with 10 to 50%-wt, relative to the nonhydrolyzed ester sulfate, of an already hydrolyzed ester sulfate, and is subsequently subjected to further hydrolysis.

7. The process according to claim 1, wherein the hydrolysis of the ester sulfate is carried out under pressure.

8. The process according to claim 1, wherein the saturated or unsaturated hydroxy fatty acid ester or oxalkylated saturated or unsaturated hydroxy fatty acid ester is an ester of a low-molecular, water-soluble, mono- or bivalent alcohol.

9. The process according to claim 1, wherein an unsaturated fatty acid is used in admixture with a saturated fatty acid ester.

10. The process according to claim 1, wherein the sulfation or hydrolysis there is used a mixture of different esters.

11. The process according to claim 1 wherein the material sulfated is a fatty acid ester substantially free from fatty acid.

12. The process according to claim 1, wherein the sulfated fatty acid esters used in hydrolysis are substantially free from cleavage products.

13. The process according to claim 1, wherein the hydrolysis is carried out with a base.

* * * * *